United States Patent
Ricketts et al.

(10) Patent No.: US 11,101,040 B2
(45) Date of Patent: Aug. 24, 2021

(54) SYSTEMS AND METHODS FOR CLINICAL VIDEO DATA STORAGE AND ANALYSIS

(71) Applicant: Hanger, Inc., Austin, TX (US)

(72) Inventors: Antony F. W. Ricketts, Reno, NV (US); Barry A. Thomson, Reno, NV (US); Zlatko L. Hodin, Reno, NV (US)

(73) Assignee: Hanger, Inc., Austin, TX (US)

( * ) Notice: Subject to any disclaimer, the term of this patent is extended or adjusted under 35 U.S.C. 154(b) by 22 days.

(21) Appl. No.: 16/389,285

(22) Filed: Apr. 19, 2019

(65) Prior Publication Data

US 2019/0326018 A1 Oct. 24, 2019

Related U.S. Application Data

(60) Provisional application No. 62/660,716, filed on Apr. 20, 2018.

(51) Int. Cl.

| | |
|---|---|
| *G06K 9/00* | (2006.01) |
| *G16H 50/20* | (2018.01) |
| *G06T 7/246* | (2017.01) |
| *G16H 30/40* | (2018.01) |
| *G16H 20/30* | (2018.01) |
| *G06T 7/00* | (2017.01) |

(52) U.S. Cl.
CPC .......... *G16H 50/20* (2018.01); *G06T 7/0012* (2013.01); *G06T 7/246* (2017.01); *G16H 20/30* (2018.01); *G16H 30/40* (2018.01)

(58) Field of Classification Search
CPC . G06T 2207/10004; G06T 2207/30164; G06T 7/246; G06T 7/0004; G06T 2207/10116; G06T 15/20; G06T 2215/16; G06T 7/20; G06T 2207/10016; G06T 2207/30196; G06T 2207/30232; G06T 7/579; A63B 2024/0053; G06K 9/00288; G06K 9/00335; G06K 9/6269; G06K 9/6272; G06K 9/00771; G06K 9/036; G16H 20/30; G16H 30/40; G16H 40/20; G16H 80/00; G06F 30/17; G06F 9/5027; G06F 21/31; H04N 7/181; H04N 5/32; H04N 5/3655; A61N 2005/1061; G01S 13/06; A63F 13/428; A63F 13/655; A63F 13/67; A61B 6/00; A61B 6/585; A61B 2034/105; A61B 5/7246
USPC ........ 382/105, 132, 218; 340/540, 584, 665; 348/77, 92
See application file for complete search history.

(56) References Cited

U.S. PATENT DOCUMENTS

| | | | | |
|---|---|---|---|---|
| 8,237,771 | B2 * | 8/2012 | Kurtz | H04N 7/147 348/14.08 |
| 9,230,157 | B2 * | 1/2016 | Bataller | G06T 7/246 |
| 10,073,600 | B1 * | 9/2018 | Sweeney | G06F 3/04845 |

(Continued)

*Primary Examiner* — Guillermo M Rivera-Martinez
(74) *Attorney, Agent, or Firm* — Foley & Lardner LLP

(57) ABSTRACT

A system includes an image capture device and one or more processors. The image capture device is configured to detect a plurality of images regarding a subject. The one or more processors are configured to receive the plurality of images, identify the subject using the plurality of images, detect a movement of the subject using the plurality of images, compare the movement to a predetermined movement pattern, generate a movement metric based on the comparison, and store, in a database, an association between a subject profile corresponding to the identified subject, the plurality of images, and the movement metric.

20 Claims, 7 Drawing Sheets

(56) References Cited

U.S. PATENT DOCUMENTS

| | | | |
|---|---|---|---|
| 2005/0251029 A1* | 11/2005 | Khamene | A61B 8/4245 600/427 |
| 2009/0110238 A1* | 4/2009 | Li | A61B 5/7292 382/103 |
| 2010/0049095 A1* | 2/2010 | Bunn | A61B 5/1123 600/595 |
| 2011/0057802 A1* | 3/2011 | Topfer | H04N 5/367 340/584 |
| 2011/0279368 A1* | 11/2011 | Klein | A63F 13/655 345/158 |
| 2011/0285622 A1* | 11/2011 | Marti | G06T 15/20 345/158 |
| 2012/0327779 A1* | 12/2012 | Gell | H04L 47/623 370/238 |
| 2013/0229511 A1* | 9/2013 | Oostendorp | H04N 7/181 348/92 |
| 2014/0015930 A1* | 1/2014 | Sengupta | G06F 21/32 348/46 |
| 2014/0347479 A1* | 11/2014 | Givon | H04N 21/4415 348/143 |
| 2014/0375493 A1* | 12/2014 | Weisenburger | G06T 7/277 342/357.3 |
| 2015/0099990 A1* | 4/2015 | Liang | G06T 7/0016 600/508 |
| 2015/0130703 A1* | 5/2015 | Ghajar | G06F 3/013 345/156 |
| 2016/0100107 A1* | 4/2016 | Nakamura | H04N 5/2256 348/77 |
| 2017/0048482 A1* | 2/2017 | Drako | H04N 21/4335 |
| 2018/0063514 A1* | 3/2018 | Mizuno | G06F 3/147 |
| 2018/0075779 A1* | 3/2018 | Tsuzuki | G09B 19/24 |

* cited by examiner

SYSTEMS AND METHODS FOR CLINICAL VIDEO DATA STORAGE AND ANALYSIS

CROSS-REFERENCE TO RELATED APPLICATIONS

The present disclosure claims the benefit of and priority to U.S. Provisional Application No. 62/660,716, titled "SYSTEMS AND METHODS FOR A CLINICAL COMMUNICATION PLATFORM," filed Apr. 20, 2018, the disclosure of which is incorporated herein by reference in its entirety.

TECHNICAL FIELD

The present disclosure relates generally to electronic clinical data communications. More particularly, the present disclosure relates to systems and methods for a clinical communication platform.

BACKGROUND

In existing systems, clinical databases may store patient data that may be useful or necessary for clinical procedures and decision making. However, it may be difficult to effectively manage large amounts of such data, particularly if an electronic health record associated with each patient requires updating at each clinical event and collaboration amongst a variety of disparate entities. In addition, it may be difficult to objectively generate assessments of actions performed by patients.

SUMMARY

At least one aspect of the present disclosure relates to a clinical video data detection and prediction system. The system can include an image capture device and one or more processors. The image capture device is configured to detect a plurality of images regarding a subject. The one or more processors are configured to receive the plurality of images, identify the subject using the plurality of images, detect a movement of the subject using the plurality of images, compare the movement to a predetermined movement pattern, generate a movement metric based on the comparison, and store, in a database, an association between a subject profile corresponding to the identified subject, the plurality of images, and the movement metric.

At least one aspect of the present disclosure relates to a method for clinical video data detection and prediction. The method includes detecting, by an image capture device, a plurality of images of a subject, receiving, by one or more processors, the plurality of images, identifying, by the one or more processors, the subject using the plurality of images, detecting, by the one or more processors, a movement of the subject using the plurality of images, comparing, by the one or more processors, the movement to a predetermined movement pattern, generating, by the one or more processors, a movement metric based on the comparison, and storing, by the one or more processors in a database, an association between a subject profile corresponding to the identified subject, the plurality of images, and the movement metric.

DETAILED DESCRIPTION

The present solution provides systems and methods for a clinical communication platform that can enable automatic, real-time collaboration for electronic clinical data objects stored in various electronic databases. Such electronic data objects may require information from a variety of disparate entities at different stages of treatment of a patient, and may require updates each time the patient interacts with a clinical entity. For example, filling out required medical forms, especially those for Medicare and insurance entities, can be a time consuming process necessitating update information from entities including office assistants, dedicated process managers, therapists, doctors, and other health care professionals. The present solution can improve the operation of electronic clinical databases by enabling such real-time updating and collaboration while automatically implementing data privacy, security, retention, and deletion protocols. The present solution can enable both real-time and asynchronous communication between entities involved in maintaining the electronic clinical data objects to improve collaboration and reduce the number of instances in which private electronic patient data may be accessed. The present solution can enable real-time collaboration among a wide variety of client devices. The present solution can enable the appropriate electronic clinical data objects to be presented to appropriate client devices at appropriate points in time, providing beneficial contextual awareness regarding the electronic clinical data objects.

Section I describes Systems and Methods for a Clinical Communication Platform with Real-Time Collaboration. Section II describes Systems and Methods for Clinical Video Data Detection and Prediction. Section III describes Computing Environments for Providing a Clinical Communication Platform with Real-Time Collaboration.

Figure 1:
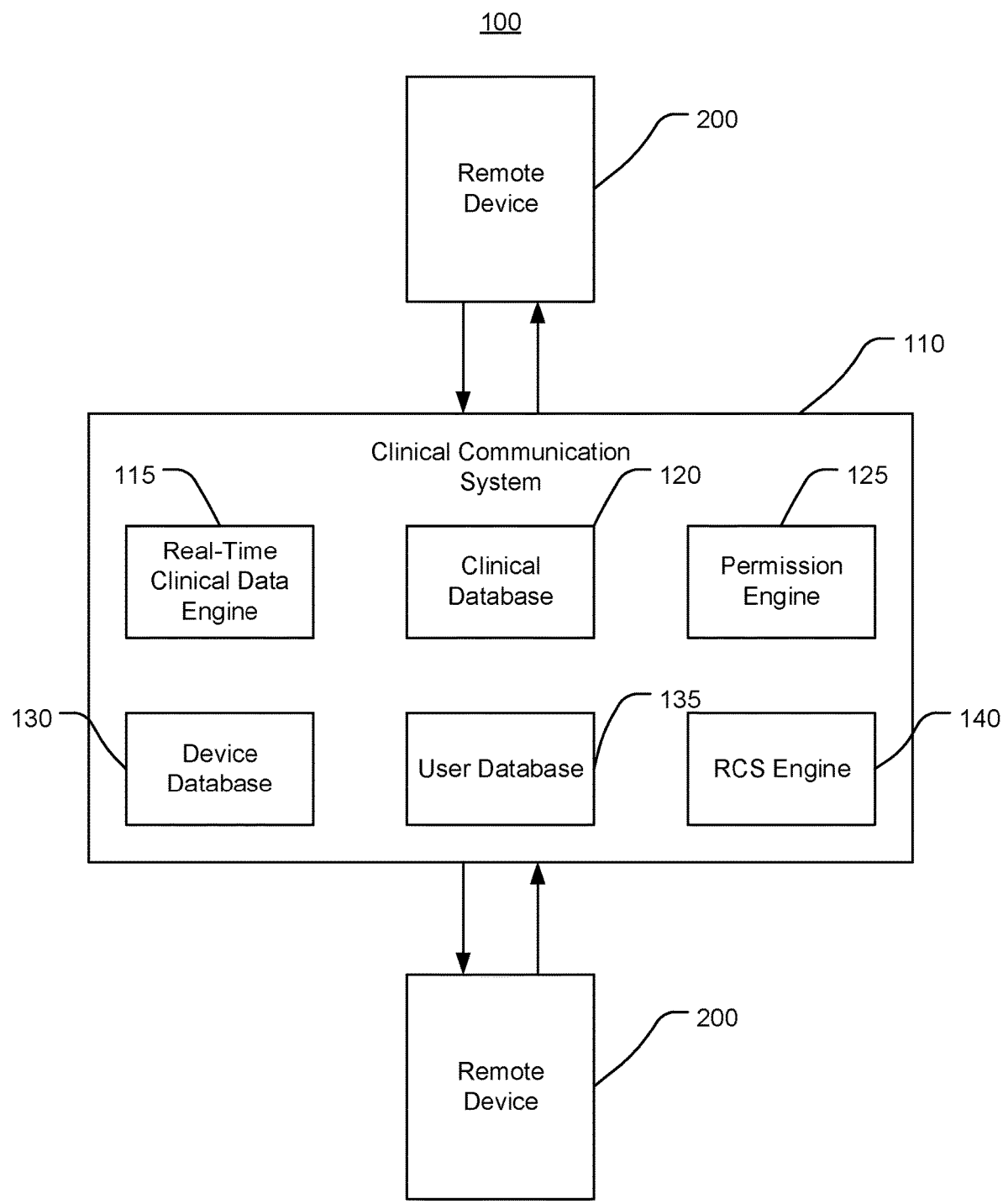
FIG. 1 is a block diagram of an embodiment of a clinical communication platform.

I. Systems and Methods for a Clinical Communication Platform with Real-Time Collaboration Referring now to FIGS. 1A-1B, a clinical communication platform 100 includes a clinical communication system 110 and a plurality of remote devices 200.

Clinical Communication System

Briefly, the clinical communication system 110 enables real-time communication regarding, and updating of, electronic clinical data objects maintained by an electronic clinical database 120 while in connection with remote devices 200. In some embodiments, the clinical communication system 200 includes a real-time clinical data engine 115, the clinical database 120, a permission engine 125, a device database 130, a user database 135, and a reimbursement calculation sheet (RCS) engine 140.

Clinical Database

The clinical database 120 stores and maintains a plurality of electronic clinical data objects. The electronic clinical data object (e.g., the plurality of clinical data fields thereof)

may correspond to a database, database table, database row, database column, electronic file, a section of memory (e.g., RAM), or other electronic data objects.

Each clinical data object is associated with a corresponding patient. Each electronic clinical data object includes a unique identifier and, in some embodiments, a plurality of clinical data fields. The unique identifier may be an identifier based on an existing patient identifier (e.g., social security number), or may be an identifier generated for use specifically by the clinical database 120.

Information stored in the plurality of clinical data fields can include information such as biographical information, such as name, sex, gender, date of birth, clinical event dates (e.g., admission, discharge), blood type, race, ethnicity, languages, marital status, contact information, addresses, medical providers, assessment records and scores, medical data sheets, treatment plans, reimbursement calculation data, and other such information.

In some embodiments, at least one electronic clinical data object may be associated with one or more users. For example, the clinical database 120 may store an access table indicating whether the user associated with the at least one electronic clinical data object has read and/or write permission with respect to the at least one electronic clinical data object. The clinical database 120 can store an indication of a modification of the electronic clinical data object by each user (e.g., by a remote device 200). As will be discussed further below, the clinical database 120 can store an indication of a modification of a particular clinical data field of the electronic clinical data object, which can be used to enable collaboration with respect to the particular clinical data field.

In some embodiments, at least one electronic clinical data object is associated with a device identifier associated with a corresponding user. For example, as will be explained further below, each remote device 200 may have a device identifier that can be used to associate the remote device 200 to the electronic clinical data object and corresponding user. Similarly, the clinical database 120 may associate electronic clinical data objects with corresponding user identifiers, enabling the clinical database 120 to track user-specific updates across devices and device sessions.

Real-Time Clinical Data Engine

The real-time clinical data engine 115 is configured to execute operations on electronic data maintained by the clinical database 120, such as based on electronic network transmissions from remote devices 200. The real-time clinical data engine 115 can receive a first network transmission from a first remote client device 200. The first network transmission can include one or more network packets. The first network transmission can include a first device identifier of the first remote client device 200. The real-time clinical data engine 115 can receive additional network transmissions from the first remote client device 200 as well as from other remote client devices 200. In some embodiments, the real-time clinical data engine 115 records a time of receipt of each network transmission.

The real-time clinical data engine 115 can extract, from the first network transmission (or any other network transmission), a first request to modify at least one clinical data field of an electronic clinical data object, such as an electronic clinical data object that has been identified (or selected) in the first network transmission. The first request can include a unique identifier of the identified electronic data object, which the real-time clinical data engine 115 can use to retrieve the identified electronic data object from the clinical database 120. The first request can include a first field identifier corresponding to a identified clinical data field, which the real-time clinical data engine 115 can use to identify the identified clinical data field. In some embodiments, the real-time clinical data engine 115 can identify the identified electronic clinical data object by at least one of (i) using the unique identifier to identify the identified electronic clinical data object from the clinical database 120 or (ii) using the first device identifier to determine the corresponding user and identify the identified electronic clinical data object associated with the corresponding user.

The first request can include a first indication of a first modified state of the identified clinical data field. The first indication can include text data, image data, and/or audio data. In some embodiments, such as where the identified clinical data field has a plurality of predetermined states (e.g., discrete values for a particular clinical parameter), the first indication may indicate a selection of a particular predetermined states. The first request can include a time of entry of the first modified state, or a time of generation of the first request (or the first network transmission), which can enable accurately prioritizing requests even if the requests are received at the clinical communication system 110 over network pathways having varying network speeds.

The real-time clinical data engine 115 can modify the identified electronic clinical data object using the first indication of the first modified state. For example, the real-time clinical data engine 115 can write a new value to the identified clinical data field of the identified electronic clinical data object based on the first indication of the first modified state, in order to modify an existing value stored in the identified clinical data field (or generate a new value for the identified clinical data field).

Permission Engine

In some embodiments, the real-time clinical data engine 115 executes the permission engine 125 to perform operations such as determining whether to modify the identified electronic clinical data object based on indications of modified states. Determining whether to modify the identified electronic clinical data object may include determining whether the remote client device 200 from which the request was received has authorization to cause the modification, as well as reconciling nearly-contemporaneous or otherwise conflicting requests from multiple devices.

In some embodiments, the permission engine 125 includes a set of policies, heuristic, or other rules for determining whether to modify the identified electronic clinical data object. The set of rules may include an access table mapping each device identifier and/or user identifier to a read permission and/or a write permission for each corresponding clinical data object. For example, the access table may indicate a that an indication of a modified state of a particular clinical data field received in a request having a particular user identifier has permission to be written to the particular clinical data field, and the real-time clinical data engine 115 can execute the permission engine 115 to determine to modify the particular clinical data field accordingly. In some embodiments, the real-time clinical data engine 115 executes the permission engine 125 based at least on the first request to determine to modify the identified electronic clinical data object (and/or the identified clinical data field thereof), such as by using device and/or user identifiers extracted from the first request. In some embodiments, the access table may be maintained by a device permission database, and the permission engine 125 can search the device permission database using the device identifier to retrieve a device flag indicating whether the corresponding remote device 200 has permission to modify the identified clinical data field of the identified clinical data object.

In some embodiments, the real-time clinical data engine 115 executes the permission engine 125 using credential information to determine to modify the identified clinical data field. The credential information can include a user identifier (e.g., user name, unique user identifier, email address) and/or user code (e.g., password, pin, key).

In some embodiments, the real-time clinical data engine 115 executes the permission engine 125 to determine which of multiple requests to modify the same clinical data field should be executed (assuming that each of the requests have write permission for the clinical data field in question by executing the permission engine 125 in the manner described above). As noted above, the real-time clinical data engine 115 can record times of receipt for each network transmission including a request to modify the particular clinical data field, such as a first time of receipt for a first network transmission including a first request and a second time of receipt for a second network transmission including a second request. The permission engine 125 can determine that a first field identifier of the first request and a second field identifier of the second request each correspond to a same identified clinical data field. In response, the permission engine 125 can compare the first time of receipt to the second time of receipt to determine which request was received first, and determine to modify the identified clinical data field based on which request was received first. For example, the permission engine 135 can determine to modify the identified clinical data field using the second indication based on the comparison indicating the second time of receipt being prior to the first time of receipt. It will be appreciated that the permission engine 125 may also use a time of entry of each modified state, or a time of generation of each network transmission, to determine which request to use for modification, which can enable accurate prioritization of requests.

In some embodiments, the permission engine 125 determines to modify the identified clinical data field using the earlier request further based on a difference between the second time of receipt and the first time of receipt being less than a threshold difference. The threshold difference can be used to ensure that subsequent updates to the identified clinical data field that are reflective of real world changes in information, rather than potentially conflicting updates received at the same time. For example, in response to receiving each request to modify a identified clinical data field, the real-time clinical data engine 115 can initiate a corresponding timer, stop the corresponding timer upon expiration of a duration of time corresponding to the threshold difference, search for additional requests received during the duration of time, identify each additional request that has a field identifier corresponding to the identified clinical data field, and select the earliest request within the duration of time to use to modify the identified clinical data field. The threshold difference may be set to be significantly longer than an expected network transmission time of the requests; for example, if the expected network transmission time is on the order of milliseconds to seconds, the threshold difference may be on the order of tens of seconds to minutes.

It will be appreciated that in some embodiments, unauthorized changes may be requested or made to electronic clinical data objects. The real-time clinical data engine 115 can execute the permission engine 125 to revert modifications responsive to detecting an unauthorized change. The real-time clinical data engine 115 can execute the permission engine 125 to parse the electronic clinical data objects (e.g., based on a modification history as described below with respect to the audit generator), identify modifications made to electronic clinical data objects, determine whether the remote device 200 was authorized to generate the request to modify the electronic clinical data object (e.g., based on an identifier and/or user credentials associated with the request). Responsive to detecting that the identified modification(s) was not authorized, the real-time clinical data engine 115 can revert the modified clinical data field(s) to a previous state (e.g., based on a previous instance of the electronic clinical data object maintained in the clinical database 120).

Device Database

In some embodiments, the clinical communication system 110 maintains information regarding remote devices 200 in the device database 130. The device database 130 may be implemented as part of and/or maintain information analogous to that of the clinical database 120. The device database 130 may maintain associations between particular remote device(s) 200 and electronic clinical data objects which have been transmitted to the particular remote device(s) and/or for which the real-time clinical data engine 115 has received and/or executed requests to modify corresponding electronic clinical data object(s). The device database 130 may maintain a record of modification requests associated with each remote device 200. The device database 130 may maintain a record of users authenticated for viewing and/or modifying corresponding electronic clinical data object(s) using the remote devices 200.

In some embodiments, the device database 130 maintains a state associated with each remote device 200. The state may include an indication of time data corresponding to when a communication link was established with the remote device 200 (e.g., a latest time of transmission to the remote device 200 or transmission received from the remote device 200). The state may include an indication of an instance of an electronic data object that the real-time clinical data engine 115 transmitted to the remote device 200 or regarding which the real-time clinical data engine 115 received a request to modify the electronic clinical data object from the remote device 200. It will be appreciated that the clinical database 120 may store similar states or instances of electronic clinical data objects, such that the real-time clinical data engine 115 can access a mapping of each instance of each electronic clinical data object to each corresponding device state (and each user associated with each corresponding instance and/or device state).

User Database

In some embodiments, the clinical communication system 110 maintains information regarding users of remote devices 200 in the user database 135. The user database 135 may be implemented as part of and/or maintain information analogous to that of the clinical database 120 and the device database 130. The user database 135 may maintain associations between electronic clinical data objects and corresponding users, such as users for whom requests to modify corresponding electronic clinical data objects have been received at the real-time clinical data engine 115, including if such requests have been authorized by the real-time clinical data engine 115. The user database 135 may maintain a record of modification requests made in association with each user. The user database 135 may maintain an association amongst users.

RCS Engine

In some embodiments, the RCS engine 140 uses information from electronic clinical data objects maintained by the clinical database 120 to calculate reimbursement information. For example, the RCS engine 140 can store a plurality of policies, heuristics, or other rules used to execute a reimbursement calculation. The real-time clinical data engine 115 can execute the RCS engine 140 to parse an electronic clinical data object, retrieve information stored in clinical data fields corresponding to the rules of the RCS engine 140, and execute the rules on the information stored in the clinical data fields to calculate a reimbursement associated with the electronic clinical data object. The RCS engine 140 can determine whether a particular clinical data field does not include information (or proper information) for performing the RCS calculation based on information stored in the particular clinical data field. In some embodiments, the RCS engine 140 is executed to classify a patient of the electronic clinical data object based on the data stored in the electronic clinical data object, and calculates the reimbursement based on the classification of the patient.

Remote/Client Device for Clinical Communication Platform

Referring further to FIG. 1B, the remote device 200 is illustrated according to an embodiment of the present disclosure. In some embodiments, the remote device 200 can incorporate features of various devices described in Section II below. For example, the remote device 200 can be implemented using personal computers/desktops, portable computers/laptops, tablets, smart phones, smart watches, autonomous reality/virtual reality devices, electronic devices having voice recognition and voice interface features, and other such devices.

The remote device 200 includes a processing circuit 210 including a processor 215 and a memory 220. In some embodiments, the processor 215 may be implemented as a specific purpose processor, an application specific integrated circuit (ASIC), one or more field programmable gate arrays (FPGAs), a group of processing components, or other suitable electronic processing components. The memory 220 is one or more devices (e.g., RAM, ROM, flash memory, hard disk storage) for storing data and computer code for completing and facilitating the various user or client processes, layers, and modules described in the present disclosure. The memory 220 may be or include volatile memory or non-volatile memory and may include database components, object code components, script components, or any other type of information structure for supporting the various activities and information structures of the inventive concepts disclosed herein. The memory 220 is communicably connected to the processor 215 and includes computer code or instruction modules for executing one or more processes described herein. The memory 220 can include various circuits, software engines, and/or modules that cause the processor 215 to execute the systems and methods described herein.

The communications interface 225 can receive and transmit electronic data transmissions. The communications interface 225 may include wired or wireless communication receivers/transmitters (e.g., a USB port, an Ethernet port, a wireless transceiver, etc.). The communications interface 225 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, the communications interface 225 can include a USB port or an Ethernet card and port for sending and receiving data via an Ethernet-based communications link or network. The communications interface 226 can include a Wi-Fi transceiver for communicating via a wireless communications network or cellular or mobile phone communications transceivers. The communications interface 225 can receive transmissions from the clinical communication system 110 for providing to the processing circuit 210 and vice versa.

In some embodiments, the remote device 200 includes a user interface 230. The user interface 230 can include a display device 235 and a user input device 240. In some embodiments, the display device 235 and user input device 240 are each components of an integral device (e.g., touchpad, touchscreen, device implementing capacitive touch or other touch inputs). The user input device may include one or more buttons, dials, sliders, keys, or other input devices configured to receive input from a user. The display device 235 may include one or more display devices (e.g., LEDs, LCD displays, etc.). The user interface 230 may also include output devices such as speakers, tactile feedback devices, or other output devices configured to provide information to a user. In some embodiments, the user input device 240 includes a microphone, and the processing circuit 210 includes a voice recognition engine configured to execute voice recognition on audio signals received via the microphone, such as for extracting commands from the audio signals.

Remote Device Clinical Communication Engine

In some embodiments, the memory 220 includes a clinical communication engine 250. In some embodiments, the clinical communication engine 250 executes an application ("app"), which may be specifically configured for execution on the remote device 200. The processing circuit 210 may be configured to communicate with a remote application storage server (e.g., application store) to receive updates for the application automatically and/or in response to user input indicating instructions to update the application. In some embodiments, the clinical communication engine 250 is configured to use an operating system of the remote device 200 for managing communications between the application and other components of the client device 200.

The clinical communication engine 250 (e.g., by executing the application) can provide a representation of an electronic clinical data object received from the clinical communication system 110 to the user interface 230 for presentation to a user. The clinical communication engine 250 can receive user inputs from the user input device 240, such as selections of clinical data fields and/or modifications to clinical data fields, and generate a request based on the received user input for transmission to the clinical communication system 110 using the communications interface 225. The clinical communication engine 250 can periodically poll the clinical communication system 110 for a particular electronic clinical data object. The clinical communication engine 250 can transmit a retrieval request to the clinical communication system 110 to retrieve an electronic clinical data object.

The clinical communication engine 250 can generate the representation of the electronic clinical data object to include an indication of collaboration features, such as clinical data fields which have been identified for editing or are being edited by other remote devices 200, messaging features, and alerts regarding messaging or particular clinical data fields to be filled out based on an indication of the user of the remote device 200, such as an indication corresponding to user credentials used to execute the application and/or retrieve electronic clinical data objects from the clinical communication system 110.

In some embodiments, the clinical communication engine 250 is configured to use user credentials (e.g., received via user input device 240 and/or maintained in memory 220) to establish a user-specific instance of the application being executed by the clinical communication engine 250. The user credentials may include one or more user identifiers (e.g., user name, unique user identifier, email address) and/or user codes (e.g., password, pin, key). The clinical communication engine 250 can transmit the user credentials to the clinical communication system 110 (e.g., when generating requests to modify electronic clinical data object(s)). The clinical communication engine 250 can similarly establish a device-specific instance of the application being executed based on an identifier of the remote device 200.

Executing the Clinical Communication Platform for Real-Time Collaboration

As discussed above, the real-time clinical data engine 115 can enable real-time collaboration, including modifying electronic clinical data objects maintained in the clinical database 120 based on requests from remote devices 200, including executing the permission engine 125 to selectively manage requests for modifying electronic clinical data objects received from remote devices 200. For example, the real-time clinical data engine 115 can enable medical forms of electronic clinical data objects to be collaboratively filled out, without locking out an entire electronic clinical data object.

In some embodiments, the real-time clinical data engine 115 can track modification of electronic clinical data objects and communicate modifications to remote devices 200, such as on a user session-specific and/or device-specific basis. The real-time clinical data engine 115 can track which clinical data field a user wants to edit. For example, the real-time clinical data engine 115 can receive an indication from the clinical communication engine 250 of a selection of a particular clinical data field, where the clinical communication engine 250 determined the selection of the particular clinical data field based on a user input received from the user input device 240 while the electronic clinical data object corresponding to the particular clinical data field is presented via display device 235. The real-time clinical data engine 115 can generate an update transmission based on the indication of the selection of the particular clinical data field, and transmit the update transmission to each remote device 200 executing an application for presenting the electronic clinical data object corresponding to the particular clinical data field.

For example, the real-time clinical data engine 115 can retrieve, from the device database 130 and/or the user database 135, an indication of which remote device(s) 200 and or users thereof may be associated with the electronic clinical data object, and store an instruction in the device database 130 to transmit the updated electronic clinical data object to the associated remote device(s) 200 responsive to detecting that electronic communication is established with the associated remote device(s). This can allow a modification being made by a user of a first remote device 200 to be pushed in real time to one or more second remote devices 200 that are also presenting representation of the electronic clinical data object, so that other users can see that the clinical data field is being viewed and/or edited. This can allow users to decide in real-time whether or not to continue editing the clinical data field.

Similarly, the real-time clinical data engine 115 can update the electronic clinical data object maintained in the clinical database 120 to include an indication of the clinical data field(s) being identified, viewed, and/or modified. As such, when the real-time clinical data engine 115 transmits the electronic clinical data object to remote device(s) 200, the remote device(s) 200 are able to inform users when the clinical data field(s) are being edited by other users.

Real-Time Communication Sessions Between Remote/Client Devices Regarding Electronic Data Objects In some embodiments, the real-time clinical data engine 115 can establish a communication session between one or more remote device(s) 200 presenting a particular electronic clinical data object, such as to allow users to collaborate by transmitting and receiving messages in real-time regarding the particular electronic clinical data object, including a particular clinical data field thereof. For example, the real-time clinical data engine 115 can receive a first message transmission associated with the particular clinical data field from a first remote device 200, extract, from the first message transmission, a recipient identifier and the first message, generate a second message transmission based on the recipient identifier and the first message, and transmit the second message transmission to a remote device 200 corresponding to the recipient identifier. The recipient identifier may include at least one of a device identifier or a user identifier, and the real-time clinical data engine 115 can use the clinical database 120, device database 130, and/or user database 135 to identify the remote device 200 to which to transmit the second message transmission.

The real-time clinical data engine 115 can generate the second message transmission to include an instance of the particular electronic clinical data object. The real-time clinical data engine 115 can generate the second message transmission to include an indication of the particular clinical data field. The clinical communication engine 250 of the first remote device 200 can generate the first message transmission in response to receiving a user input via user input device 240 indicating instructions to transmit the first message transmission. The user input may be an input identifying a particular display object associated with messaging, such as a message icon. The clinical communication engine 250 can present the representation of the electronic clinical data object with message icon(s) in proximity to clinical data fields, allowing a user to easily initiate a communication session corresponding to a particular clinical data field.

Real-Time Minimum Data Set Collaboration

In some embodiments, the real-time clinical data engine 115 can enable real-time collaboration for filling out electronic clinical data objects that include minimum data set (MDS) forms. The real-time clinical data engine 115 can provide transmissions to two or more remote devices 200 that include an MDS electronic clinical data object. The real-time clinical data engine 115 can receive a first request to modify an identified clinical data field of the MDS electronic clinical data object from a first remote device 200, and modify the MDS electronic clinical data object maintained in the clinical database 120 based on the first request.

In some embodiments, in response to modifying the MDS electronic clinical data object maintained in the clinical database 120, the real-time clinical data engine 115 can generate an output transmission for transmitting the modifying MDS electronic clinical data object to one or more second remote devices 200 (e.g., second remote devices 200 which are presenting the same MDS electronic clinical data object, which are indicated to be associated with the same MDS electronic clinical data object based on device identifiers and/or user identifiers, etc.). In some embodiments, the real-time clinical data engine 115 can include an indication of an instruction for a user of a particular remote device 200 to modify a particular clinical data field, so that the particular remote device 200 presents the MDS electronic clinical data object with the instruction.

Real-Time RCS Collaboration

In some embodiments, the real-time clinical data engine 115 can enable real-time collaboration for performing RCS calculations using electronic clinical data objects. The real-time clinical data engine 115 can execute the RCS engine 140 to perform an RCS calculation using an electronic clinical data object. In some embodiments, the real-time clinical data engine 115 can detect missing information of the electronic clinical data object based on executing the RCS engine 140. For example, when executing the RCS engine 140, the real-time clinical data engine 115 can determine that a particular electronic clinical data field of the electronic clinical data object does not include a value, text string, or other information on which to execute an RCS calculation rule. In response to detecting missing information, the real-time clinical data engine 115 can at least one of (1) associate an alert condition with one or more users associated to the particular clinical data field of the electronic clinical data object in the clinical database 120 and/or the user database 135, or (2) transmit an alert to a remote device 200 corresponding to the particular clinical data field based on information maintained in the device database 130 (or the clinical database 120 or user database 135), so that a user is alerted to the need to fill out the particular clinical data field in order for the RCS calculation to be completed.

Alert Generator for Real-Time Clinical Data Engine

The real-time clinical data engine 115 can use the clinical database 120 to maintain indications of whether electronic clinical data objects need information to be entered. For example, the real-time clinical data engine 115 can associate an event engine (e.g., an engine configured to generate a response to an event such as a change in a property, a function being executed, an electronic clinical data object being created or deleted, a time-based condition) with one or more clinical data fields of each electronic clinical data object. In some embodiments, the real-time clinical data engine 115 initiates each event engine in response to a trigger condition, such as an initial generation of the electronic clinical data object, an indication of a medical event (e.g., a patient visiting a medical facility), or a modification to a different clinical data field. The real-time clinical data engine 115 can periodically compare each event to a corresponding threshold or other condition to determine whether an alert condition has been satisfied (e.g., when the event has exceeded a corresponding time threshold). In some embodiments, the real-time clinical data engine 115 uses multiple thresholds for each one or more clinical data fields, such as to provide alerts of progressive importance or urgency. In some embodiments, a threshold may be associated with a value state change, such that the real-time clinical data engine 115 can cause a fine or reimbursement change to be associated with the electronic clinical data object by detecting the value state change. For example, in response to detecting that the threshold associated with a reimbursement change has been exceeded, the real-time clinical data engine 115 can modify one or more rules of the RCS engine 140 associated with the electronic clinical data object so that when the real-time clinical data engine 115 executes the RCS engine 140 using the electronic clinical data object, the reimbursement calculation will be modified.

In some embodiments, in response to determining that the alert condition has been satisfied, the real-time clinical data engine 115 can identify a user associated with the one or more clinical data fields, and at least one of 1) associate an alert condition with one or more users associated to the particular clinical data field of the electronic clinical data object in the clinical database 120 and/or the user database 135, or (2) transmit an alert to a remote device 200 corresponding to the particular clinical data field based on information maintained in the device database 130 (or the clinical database 120 or user database 135), so that a user is alerted to the need to fill out the particular clinical data field. As such, there may be a targeted alert sent out to just those user(s) needed to complete the electronic clinical data object.

In some embodiments, in response to determining that the alert condition has been satisfied, the real-time clinical data engine 115 can modify a responsibility condition associated with the one or more clinical data fields. For example, the user database 135 may store associations between each user and corresponding managers or other associated users. The real-time clinical data engine 115 can generate and transmit an alert to each user (e.g., each remote device 200 associated with each user) associated with the user for which the alert condition was satisfied. In some embodiments, the alert can include a request to modify a user associated with the one or more clinical data fields for which the alert condition was generated; after transmitting the alert, the real-time clinical data engine 115 can receive an indication of the user modification request from the remote device 200, and modify the user(s) associated with the one or more clinical data fields (e.g., in the user database 135 and/or clinical database 120). The real-time clinical data engine 115 can reinitialize the timer associated with the one or more clinical data fields responsive to modifying the user(s), and/or modify threshold times for alert generation responsive to modifying the user(s).

Audit Generator for Real-Time Clinical Data Engine

The real-time clinical data engine 115 can maintain, for each electronic clinical data object in the clinical database 120, a record of each modification to the electronic clinical data object. The record can include an indication of at least one of the user associated with the application executed by the clinical communication engine 250 from which the modification request was generated, the remote device 200 associated with the application executed by the clinical communication engine 250 from which the modification request was generated, and/or a time at which the modification request was generated by the clinical communication engine 250. In response to receiving an audit request (e.g., from remote device 200) based on one or more of the parameters of the indication enumerated above, the real-time clinical data engine 115 can generate an audit and transmit the audit to the requesting entity.

Conversation Thread Generator for Real-Time Clinical Data Engine

In some embodiments, the real-time clinical data engine 115 maintains a conversation object associated with each electronic clinical data object. The conversation object can include each message received from/transmitted to each remote device 200 associated with the electronic clinical data object. In some embodiments, the real-time clinical data engine 115 specifically associates each message to each clinical data field. The real-time clinical data engine 115 can update each conversation object responsive to receiving messages associated with the conversation object (e.g., based on a communication session established between remote devices 200).

In some embodiments, the real-time clinical data engine 115 adds or removes users to conversation objects; for example, the real-time clinical data engine 115 can receive a user add/removal request from one of the remote devices 200, extract an identifier of the user to be added/removed from the add/removal request, and update the associations of user(s) the conversation object using the identifier. As such, a new user can quickly come to speed on contextual information regarding the electronic clinical data object associated with the conversation object. In some embodiments, the real-time clinical data engine 115 associates users (e.g., user profiles of users as stored in the user database 135) to the conversation object. In some embodiments, the real-time clinical data engine 115 automatically associates users to conversation objects based on users associated to the electronic clinical data object corresponding to the conversation object in the user database 135, so that, for example, as teams change (based on which the real-time clinical data engine 115 can update the user database 135), existing users may be removed from particular conversation objects and new users may be added thereto.

In some embodiments, message transmissions received by the real-time clinical data engine 115 from remote devices 200 include one or more tags associated with each message. The tags may correspond to clinical data fields and/or users. The real-time clinical data engine 115 can execute a search based on tags to identify various messages and/or conversation objects associated with the tags, and provide a conversation object corresponding to identified tags to remote devices 200.

In response to receiving a user request for a particular conversation object, the remote device 200 can generate and transmit a conversation object request to the real-time clinical data engine 115, which the real-time clinical data engine 115 can receive, identify the particular conversation object from, and in response transmit a conversation object transmission to the remote device 200. The remote device 200 can then present a representation of the conversation object to the user via the display device 235.

Figure 3:
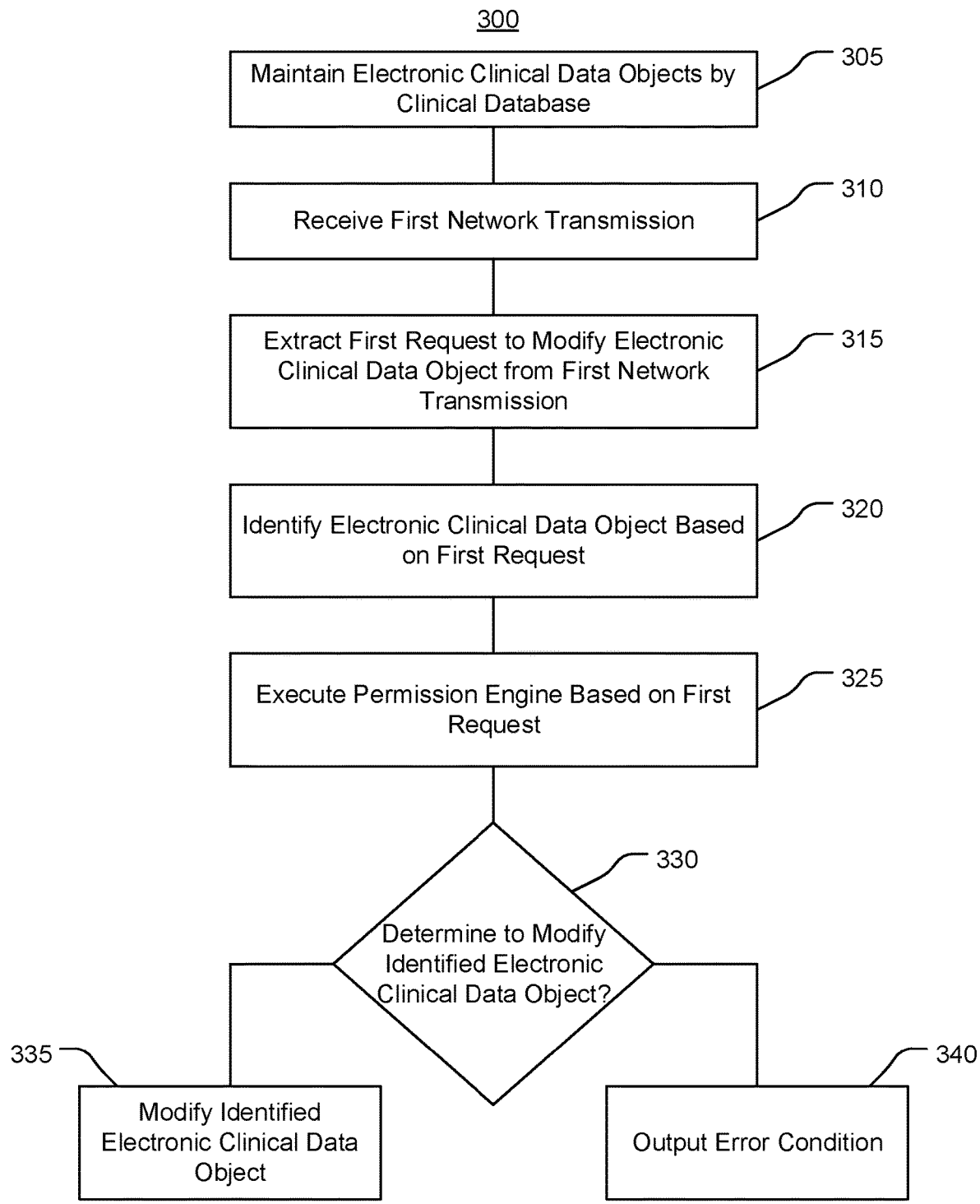
FIG. 3 is a flow diagram of an embodiment of a method for executing a clinical communication platform.

Referring now to FIG. 3, a method 300 for executing a clinical communication platform is shown according to an embodiment of the present disclosure. The method 300 can be implemented by various devices and systems described herein, such as the clinical communication system 200.

At 305, a plurality of electronic clinical data objects is maintained by a clinical database. Each electronic clinical data object is associated with a patient. Each electronic clinical data object includes a unique identifier, and can include a plurality of clinical data fields. In some embodiments, at least one electronic clinical data object is associated with a device identifier, which may be associated with a corresponding user.

At 310, a real-time clinical data engine receives a first network transmission from a first remote device. The first network transmission can include a first device identifier of the first remote device.

At 315, the real-time clinical data engine extracts a first request to modify an electronic clinical data object from the first network transmission. Extracting the first request can include extracting (i) a unique identifier of the identified electronic clinical data object, (ii) a first field identifier corresponding to a particular clinical data field, and (iii) a first indication of a first modified state of the particular clinical data field.

At 320, the real-time clinical data engine identifies the electronic clinical data object based on the first request. Identifying the identified electronic clinical data object can include at least one of (i) using the unique identifier to identify the identified electronic clinical data object from the clinical database or (ii) using the first device identifier to determine the corresponding user and identify the identified electronic clinical data object associated with the corresponding user.

At 325, the real-time clinical data engine executes a permission engine based on the first request to determine, at 330, whether to modify the identified electronic clinical data object. Executing the permission engine can include using the first request to determine whether the first request (e.g., based on a device identifier, user identifier, credentials, or other features thereof) is authorized to cause the real-time clinical data engine to modify the identified electronic clinical data object.

At 335, responsive to determining to modify the identified electronic clinical data object, the real-time clinical data engine modifies the identified electronic clinical data object. Modifying the identified electronic clinical data object can include identifying the identified clinical data field using the first field identifier and modifying the particular clinical data field of the identified electronic clinical data object stored in the clinical database using the first indication of the first modified state. In some embodiments, the real-time clinical data engine transmits the modified electronic clinical data object to the first remote device as well as to one or more second remote device(s) associated with the electronic clinical data object.

At 340, responsive to determining to not modify the identified electronic clinical data object, the real-time clinical data engine outputs an error condition. Outputting the error condition may include stepping to or listening for a new request to modify one or more electronic data objects stored in the clinical database. Outputting the error condition can include generating an indication that the first request is not authorized to modify the identified electronic clinical data object, and transmitting the indication to the first remote device.

II. Systems and Methods for Clinical Video Data Detection and Prediction

Figure 2:
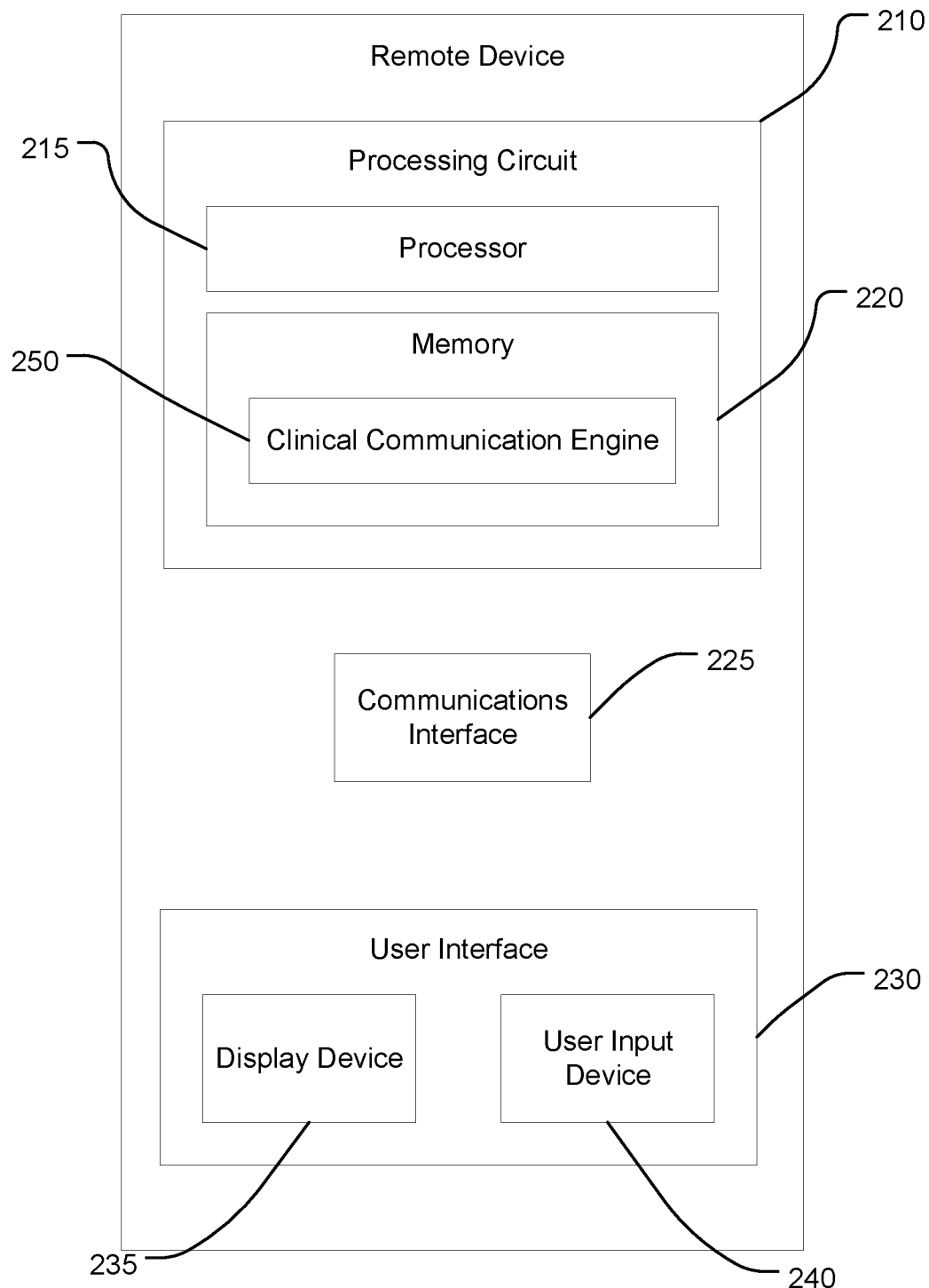
FIG. 2 is a detailed block diagram of an embodiment of a remote device of the clinical communication platform of FIG. 1.
Figure 4:
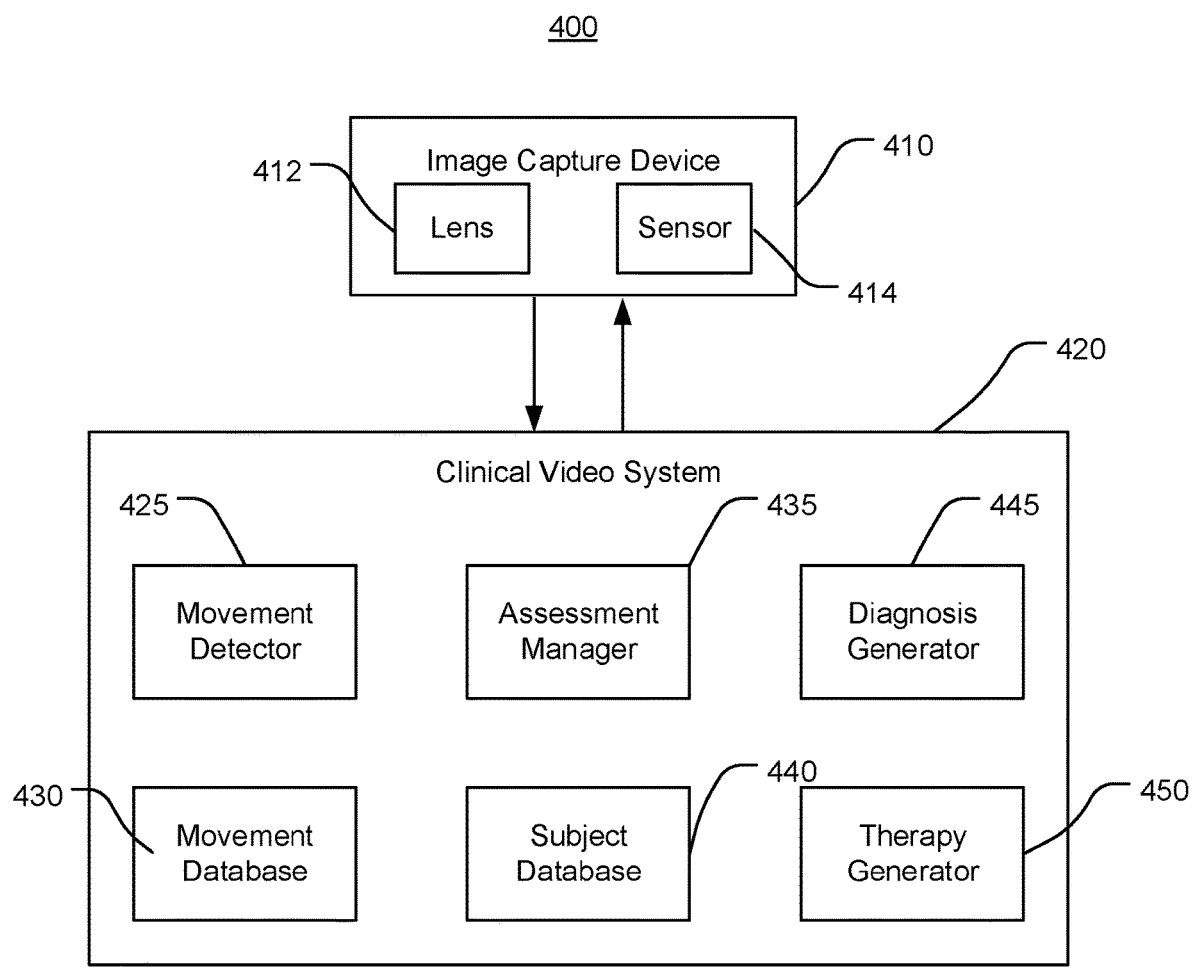
FIG. 4 is a block diagram of an embodiment of a clinical video data detection and prediction system.

Referring now to FIG. 4, a system 400 for clinical video data detection and prediction is illustrated according to an embodiment of the present disclosure. The system 400 can incorporate features of the system 100 described with reference to FIG. 1 and/or the remote device 200 described with reference to FIG. 2. The system 400 can be used to process images captured of movements performed by a subject (e.g., patient) to detect the movements. The system 400 can measure parameters of the movements, such as a distance an arm or leg travelled, or a number of times a movement is performed in a particular duration of time. The system 400 can compare the detected movements to predetermined movement patterns, which may be associated with the subject, to identify normal or abnormal movements. The system 400 can generate expected diagnoses, predict expected completion of therapy procedures, and recommend adjustments to therapy procedures, based on the detected movements. The system 400 can automatically generate information regarding the assessment, such as text data to assign to electronic data structures or forms for the subject. By directly processing video data regarding the movement, rather than relying on subjective evaluations of movements, the system 400 can more objectively and accurately detect movements, and in turn characterize movements to generate more objective and accurately predictions and therapy recommendations.

Image Capture Device

The system 400 can include at least one image capture device 410. The image capture device 410 can detect a plurality of images of a subject, such as a patient performing movements associated with an assessment. The image capture device 410 can be a camera, such as a video camera. The image capture device 410 can be implemented by the remote device 200. For example, the image capture device 410 can be a video camera of a portable electronic device. The at least one image capture device 410 can include a plurality of image capture devices 410 that are located in different positions, such as to capture images of the subject from a plurality of orientations. For example, one or more image capture devices 410 can be positioned about the subject, and can transmit detected images to a receiving device (e.g., via WiFi, Bluetooth, or other communication protocols).

The image capture device 410 can include at least one lens 412 and at least one sensor 414. The lens 412 can receive light (e.g., corresponding to a field of view of the lens 412) and provide the received light to the sensor 414. The sensor 414 can receive the light provided by the lens 412 and generate one or more images based on the received light. For example, the sensor 414 can include at least one of a charged coupled device (CCD) sensor or a complementary metal-oxide-semiconductor (CMOS) sensor.

In some embodiments, the image capture device 410 can receive user inputs regarding control of the image capture device 410. For example, the image capture device 410 can receive user inputs regarding starting, stopping, or pausing recording of images (e.g., recording video), including to record a duration of the detected movement. The image capture device 410 can receive a user input indicating a count of repetitions.

Clinical Video System

The system 400 can include a clinical video system (CVS) 420. The CVS 420 and functions thereof can be performed by various devices. For example, the CVS 420 can be implemented by the remote device 200 (e.g., the same device implementing the image capture device 410) or a device remote from the image capture device 410, such as a server, which can receive the plurality of images and process the plurality of images.

The CVS 420 can identify the subject. For example, the CVS 420 can receive an identifier of the subject, such as from a user interface coupled with the CVS 420. In some embodiments, the CVS 420 identifies the subject using the plurality of images. For example, the CVS 420 can execute a facial recognition algorithm using the plurality of images to identify the subject. The facial recognition algorithm can process the plurality of images to identify one or more facial features, and compare the identified one or more facial features to one or more facial feature templates associated with each of a plurality of subjects (e.g., maintained in subject database 440)

Movement Detector

The CVS 420 can include a movement detector 425. The movement detector 425 can receive the plurality of images from the image capture device 410. The movement detector 425 can perform various image processing algorithms, such as object recognition algorithms, to detect movements of the subject using the plurality of images. The movement detector 425 can identify features of the subject from each of the images, such as pixel(s) indicating colors, shapes, edges, contrast between pixels or groups of pixels, and spatial relationships between pixels.

In some embodiments, the movement detector 425 identifies features corresponding to anatomical features of the subject using the plurality of images. For example, the movement detector 425 can identify a candidate feature corresponding to a hand of the subject, compare the candidate feature to a plurality of templates of anatomical features (e.g., templates of hands, arms, legs, etc.), and identify the anatomical feature based on the comparison, such as if a match score of the comparison satisfies a comparison threshold. The movement detector 425 can retrieve the plurality of templates from a template database, such as a template database of subject database 440. For example, the subject database 440 may include templates that have been generated based on historical images of the subject, enabling the movement detector 425 to precisely detect features of the subject using the templates.

In some embodiments, the movement detector 425 detects the movement by tracking at least one pixel corresponding to the identified feature across at least a subset of the plurality of images. For example, the movement detector 425 can identify one or more tracked pixels corresponding to the identified feature (e.g., corresponding to a hand of the subject) in a first image of the plurality of images, and process at least one second image of the plurality of images to identify at least one of the one or more tracked pixels.

The movement detector 425 can generate an indication of the movement. The indication of the movement can include a path of the movement, such as a plurality of positions corresponding to the movement, which can correspond to pixels identified as matching the movement (e.g., pixels tracked across the plurality of images). In some embodiments, the movement detector 425 reduces a number of positions corresponding to the movement, such as by interpolating between at least two positions of the plurality of positions, which can reduce computational demand for processing the movement. In some embodiments, the movement detector 425 indicates a distance of the movement, such as a distance from a start position to an end position of the movement. The movement detector 425 may determine the distance of the movement by comparing a pixel distance between a first pixel position (e.g., x-y coordinate of a matrix of pixels forming an image of the plurality of images) of the start position and a second pixel position of the end position, and applying a calibration factor to the pixel distance. The calibration factor can be determined based on calibration of the image capture device 410 (e.g., by providing the image capture device 410 or the CVS 420 a known size dimension of an object in a field of view of the image capture device 410, or by using a position sensor of the image capture device 410 to provide the image capture device 410 an indication of a size dimension of objects in images captured by the image capture device 410 based on motion of the image capture device 410). In some embodiments, the movement detector 425 determines a count of the movement, such as a number of times the movement is performed in a predetermined duration of time based on tracking pixels corresponding to an anatomical feature of the subject. The movement detector 425 can determine an angle of the movement (e.g., an angle defined by the start position, end position, and a plane that includes the start position and is parallel to ground). The movement detector 425 can determine an arc subtended by the movement based on the path of the movement. The movement detector 425 can determine a rate of the movement based on one or more timestamps of the plurality of images and the positions of the anatomical feature tracked through the plurality of images.

The movement detector 425 can retrieve, from a movement database 430, a plurality of predetermined movement patterns, such as template movements. The plurality of predetermined movement patterns may correspond to expected movements to be performed by a subject undergoing an assessment, such as sitting down, standing up, reaching with arms, raising arms or legs, etc. The predetermined movement patterns can indicate parameters such as distance of movement, count of movement, anatomical features used to perform the movement, angle of movement, rate of movement, or other such parameters that the movement detector 425 can determine regarding the movement.

In some embodiments, the movement database 430 includes predetermined movement patterns assigned to at least one particular subject. For example, the predetermined movement patterns may be generated (e.g., by CVS 420) using historical images regarding movements performed by the subject. This can enable the CVS 420 to perform a longitudinal evaluation of the movements of the particular subject.

The movement detector 425 can compare the detected movement to at least one predetermined movement pattern to determine whether the detected movement matches the at least one predetermined movement pattern. For example, the movement detector 425 can compare the detected movement to an arm movement pattern and a leg movement pattern to determine whether the detected movement is an arm movement or a leg movement. The movement detector 425 can use various parameters of the detected movement as discussed above (e.g., identifier of anatomical feature, distance, count, angle, rate, etc.) to compare to corresponding parameters of the predetermined movement pattern. The movement detector 425 can generate a match score based on the comparison. The movement detector 425 can determine the detected movement to match the predetermined movement pattern responsive to the match score satisfying a match threshold.

In some embodiments, the movement detector 425 determines a movement metric based on the comparison. For example, the predetermined movement pattern can be a desired pattern for the corresponding movement (e.g., a desired range of motion of a limb of the subject); by comparing the detected movement to the predetermined movement pattern, the movement detector 425 can determine a movement metric that can indicate how well the detected movement matches the movement that the subject should be performing based on the predetermined movement pattern. In some embodiments, the movement metric can include a parameter of the detected movement, such as distance, count, or rate. In some embodiments, the movement detector 425 determines the movement metric based on the detected movement (e.g., without comparing to the predetermined movement pattern), such as to determine distance, rate, or count parameters of the movement.

The movement detector 425 can store, in the subject database 440, an association between a subject profile of the identified subject, the detected movement, and the movement metric. For example, the movement detector 425 can use an identifier of the subject (e.g., determined via user input or facial recognition) to retrieve the subject profile, and assign the detected movement and movement metric to corresponding fields of the subject profile.

In some embodiments, the movement detector 425 provides feedback indicating instructions regarding operation of the image capture device 410, which can be used to improve the information content of the images captured by the image capture device 410 and processed by the movement detector 425 (or by other components of the CVS 420). For example, the movement detector 425 can determine a direction of the movement including an angle of the movement, compare the direction to a target direction, and generate an instruction based on a difference between the determined direction and the target direction. For example, the movement detector 425 may be able to most effectively evaluate images of an arm movement where the arm moves in a plane perpendicular to a line of sight of the image capture device 410. If the image capture device 410 is oriented such that the arm movement does not occur in a plane perpendicular to the line of sight of the image capture device 410, the movement detector 425 can provide instructions regarding adjusting at least one of the position or orientation of the image capture device 410 by comparing the direction of the arm movement to a target direction in which the arm movement would occur in the plane perpendicular to the line of sight. The movement detector 425 can similarly generate feedback indicating instructions to adjust at least one of the position or orientation of the image capture device 410 based on an orientation of the subject detected using the plurality of images from the image capture device 410.

Assessment Manager

The CVS 420 can include an assessment manager 435. The assessment manager 435 can maintain instructions regarding an assessment to be performed based on movements of the subject. For example, as described further herein, the assessment manager 435 can maintain instructions regarding assessments such as functional reach, sit to stand, and timed up and go assessments. The instructions can indicate one or more movements to be performed for each assessment.

The subject database 440 can maintain an assessment data structure for each subject. The assessment data structure can include a plurality of fields, such as type of assessment, type of movement, and biographical data regarding the subject (e.g., age, sex, height, weight). The assessment manager 435 can store movement data from the movement detector 425 using the assessment data structure.

In some embodiments, the assessment manager 435 automatically generates text data regarding the detected movement to store in the assessment data structure. For example, the assessment manager 435 can identify at least one field of the plurality of fields corresponding to the movement, generate an indication of the movement that includes at least one text string, and assign the indication of the movement to the identified at least one field. The assessment manager 435 can generate the at least one text string based on the plurality of images. For example, the assessment manager 435 can generate the at least one text string based on the detected movement data detected by the movement detector 425, such as the detected movement or the movement metric. The assessment manager 435 can generate the at least one text string based on features identified from the plurality of images (e.g., detected anatomical features). As such, the assessment manager 435 can generate suggested text that a In some embodiments, the assessment manager 435 generates the at least one text string based on an identifier of a user operating the CVS 420 (e.g., via remote device 200). For example, the assessment manager 435 can maintain a database mapping text data used to annotate assessment reports to the movements being described, such that the assessment manager 435 can generate the at least one text string using the detected movement and the database to retrieve corresponding text data. The assessment manager 435 can automatically generate template reports based on the database and the detected movement.

Diagnosis Generator

The CVS 420 can include a diagnosis generator 445. The diagnosis generator 445 can predict a diagnosis of the subject based on at least one of the detected movement or the movement metric. The diagnosis generator 445 can compare the movement metric to one or more thresholds corresponding to the detected movement, and predict the diagnosis based on the comparison. In some embodiments, the diagnosis generator 445 identifies the one or more thresholds by retrieving the one or more thresholds from a condition database (e.g., health condition database, physiological condition database) that maps movement types to conditions and maps conditions to respective one or more thresholds.

Therapy Generator

The CVS 420 can include a therapy generator 450. The therapy generator 450 can use movement data, such as detected movements or movement metrics, generated by the movement detector 425 to generate recommendations regarding movements to be performed by the subject. The therapy generator 450 can also use predicted diagnoses generated by the diagnosis generator 445 to generate recommendations regarding movements to be performed.

For example, the therapy generator 450 can determine a difference between a detected movement and a desired movement (e.g., based on the comparison between the detected movement and the predetermined movement pattern), and based on the difference, identify the recommended movement from a therapy model mapping recommended movements to differences between the detected movements and desired movements. The CVS 420 can generate the therapy model using predetermined policies regarding therapies to be performed. The CVS 420 can generate the therapy model using historical data mapping at least one of a detected movement or a movement to the recommended movements.

As discussed herein, the CVS 420 can detect movements from images captured by the image capture device 410, and associate the captured images with subject profiles in the subject database 440. The CVS 420 can similarly associate predicted diagnoses and recommendations regarding movements to be performed with respective subject profiles. As such, the CVS 420 can detect changes in movements performed by subjects over time, and use the detected changes to modify the predicted diagnoses or recommended movements. For example, the CVS 420 can update the therapy model based on images captured subsequent to the subject performing the recommended movements. In addition, because the CVS 420 uses images captured directly to detect the performed movements, the CVS 420 can more objectively identify relationships between detected movements, diagnoses, and recommended movements and update the therapy model accordingly.

In some embodiments, the CVS 420 generates presentation data regarding the detected movement. For example, the CVS 420 can generate a visual overlay to be used to present the detected movement as an overlay on previous image (e.g., previous video) of the subject performing the detected movement. The CVS 420 can generate the presentation data based on the tracked pixels used to detect the movement. For example, the CVS 420 can retrieve, from the subject database 440, one or more previous images representing a previous movement of the subject, and generate a visual representation comparing the movement detected by the movement detector 425 to the previous movement. In some embodiments, the CVS 420 uses timestamps of the movements to align the visual representation with the one or more previous images.

In some embodiments, the CVS 420 can predict how long a therapy regimen would take to produce a desired result for the therapy of the subject. For example, the CVS 420 predict completion of a target condition of the subject corresponding to the movement based on the movement metric generated by the movement detector 425. The CVS 420 can compare the movement metric to an expected value of the movement metric at which the therapy regimen is completed to determine the time to completion of the therapy regimen.

Model Training and Updating

The CVS 420 can train and update machine learning models based on data generated by the movement detector 425, assessment manager 435, diagnosis generator 445, and therapy generator 450. For example, the CVS 420 can use training data including input data (e.g., data regarding subjects) and corresponding output parameters (e.g., movement data, diagnoses, therapy parameters) to train the parameter model by providing the input data as an input to the parameter model, causing the parameter model to calculate a model output based on the input data, comparing the model output to the output parameters of the training data, and modifying the parameter model to reduce a difference between the model output and the output parameters of the training data (e.g., until the difference is less than a nominal threshold). For example, the CVS 420 can execute an objective function (e.g., cost function) based on the model output and the output parameters of the training data.

The parameter model can include various machine learning models that the CVS 420 can train using training data and/or the movement database 430 and subject database 440. The analytics engine 420 can execute supervised learning to train the parameter model. In some embodiments, the parameter model includes a classification model. In some embodiments, the parameter model includes a regression model. In some embodiments, the parameter model includes a support vector machine (SVM). In some embodiments, the parameter model includes a Markov decision process engine. In some embodiments, the parameter model includes a neural network. The neural network can include a plurality of layers each including one or more nodes (e.g., neurons, perceptrons), such as a first layer (e.g., an input layer), a second layer (e.g., an output layer), and one or more hidden layers. The neural network can include characteristics such weights and biases associated with computations that can be performed between nodes of layers, which the CVS 420 can modify to train the neural network. In some embodiments, the neural network includes a convolutional neural network (CNN).

The CVS 420 can train the parameter model by providing input from the training data, movement database 430, or subject database 440 as an input to the parameter model, causing the parameter model to generate model output using the input, modifying a characteristic of the parameter model using an objective function (e.g., loss function), such as to reduce a difference between the model output and the and the corresponding output of the training data. In some embodiments, the CVS 420 executes an optimization algorithm that can modify characteristics of the parameter model, such as weights or biases of the parameter model, to reduce the difference. The CVS 420 can execute the optimization algorithm until a convergence condition is achieved (e.g., a number of optimization iterations is completed; the difference is reduced to be less than a threshold difference).

Functional Reach

The CVS 420 can be used to detect and evaluate movements associated with a functional reach assessment, which can be used to identify balance impairments or changes in balance over time. For example, the CVS 420 can present instructions regarding performing a functional reach assessment in which the subject performs a movement to indicate a difference between the length of the arm of the subject and a maximal forward reach using a fixed base of support. The CVS 420 can use the image capture device 410 to capture a plurality of images of the movement, and use the movement detector 425 to detect the movement using the plurality of images. The CVS 420 can generate a movement metric regarding the detected movement, such as a distance the arm of the subject moves.

Sit to Stand

The CVS 420 can be used to detect and evaluate movements associated with a sit to stand assessment, which can be used to assess lower extremity function, such as to predict subsequent development of disability because it reflects the effects of chronic disease, coexisting conditions, and overall physiologic decline. For example, the CVS 420 can present instructions regarding performing a sit to stand assessment when in which a number of repetitions of a sit to stand movement being performed (e.g., five repetitions of standing up from a sitting position). The CVS 420 can generate movement metrics based on a plurality of images detected by the image capture device 410 such as a duration of time in which the movement is performed, or an extent of the movement.

Timed Up and Go

The CVS 420 can be used to detect and evaluate movements associated with a timed up and go assessment. For example, the CVS 420 can present instructions for an assessment in which the subject stands up from a chair, walks a distance of ten feet, walks back to the chair, and sits down. The CVS 420 can use the plurality of images to detect movement metrics such as a duration of time used to perform the movement.

Figure 5:
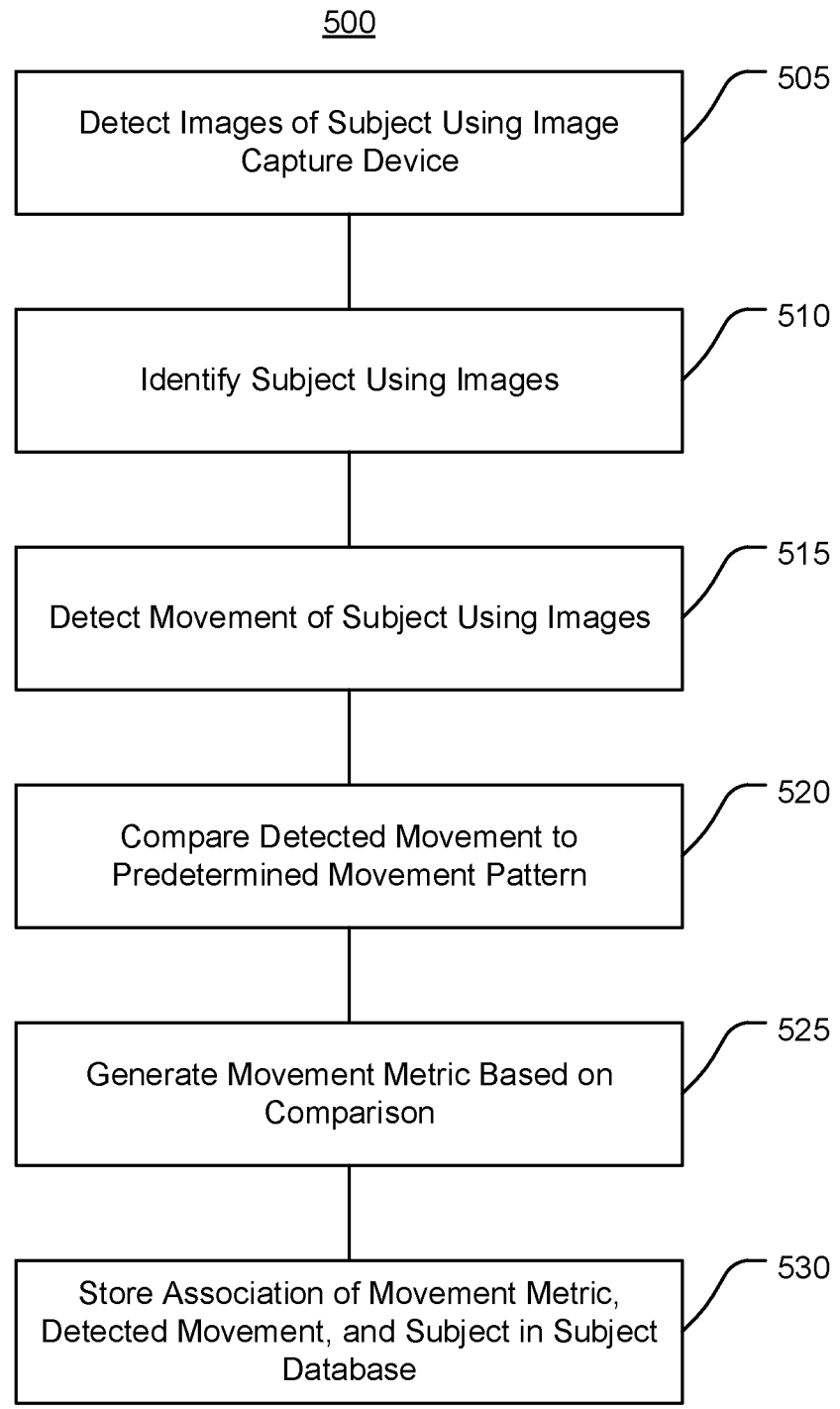
FIG. 5 is a flow diagram of an embodiment of a method for performing clinical video data detection and prediction.

Referring now to FIG. 5, a method 500 is illustrated according to an embodiment of the present disclosure. The method 500 can be performed by various systems and devices described herein, such as the system 400.

At 505, a plurality of images of a subject can be captured using an image capture device. For example, the images can be detected using a camera, such as a video camera. The plurality of images can be associated with timestamps indicating a time of detection of the images.

At 510, a subject can be identified using the plurality of images. The subject can be identified based on user input indicating the subject, such as user input received via an assessment tool executing on an electronic device. The subject can be identified using a facial recognition algorithm that identifies one or more facial features of the subject from the plurality of images and compares the identified facial features to template facial features maintained in a subject database.

At 515, a movement of the subject can be identified using the plurality of images. The movement can be identified by identifying features of the subject in the plurality of images and tracking the identified features across the plurality of images. For example, at least one anatomical feature of the subject can be identified from at least one image based on a template of the anatomical feature. At least one pixel corresponding to the anatomical feature can be tracked across the plurality of images to identify the movement. In some embodiments, identifying the movement can include at least one of generating a distance, a rate, a duration, or an angle of the movement.

At 520, the detected movement can be compared to a plurality of predetermined movement patterns. The plurality of predetermined movement patterns may correspond to expected movements to be performed by a subject undergoing an assessment, such as sitting down, standing up, reaching with arms, raising arms or legs, etc. The predetermined movement patterns can indicate parameters such as distance of movement, count of movement, anatomical features used to perform the movement, angle of movement, rate of movement, or other such parameters that can be determined regarding the movement.

At 525, a movement metric can be generated based on the comparison. The movement metric can indicate how well the detected movement matches the predetermined movement pattern. In some embodiments, the movement metric can include a parameter of the detected movement, such as distance, count, or rate.

At 530, an association of the movement metric, detected movement, and subject can be stored in a subject database. For example, a subject profile can be assigned the movement metric and the detected movement, along with a timestamp corresponding to a time at which the assessment is performed. The association can be used to monitor changes in the movement metric as a function of time, such as to generate diagnoses or predict completion of therapy regimens.

Figure 6A:
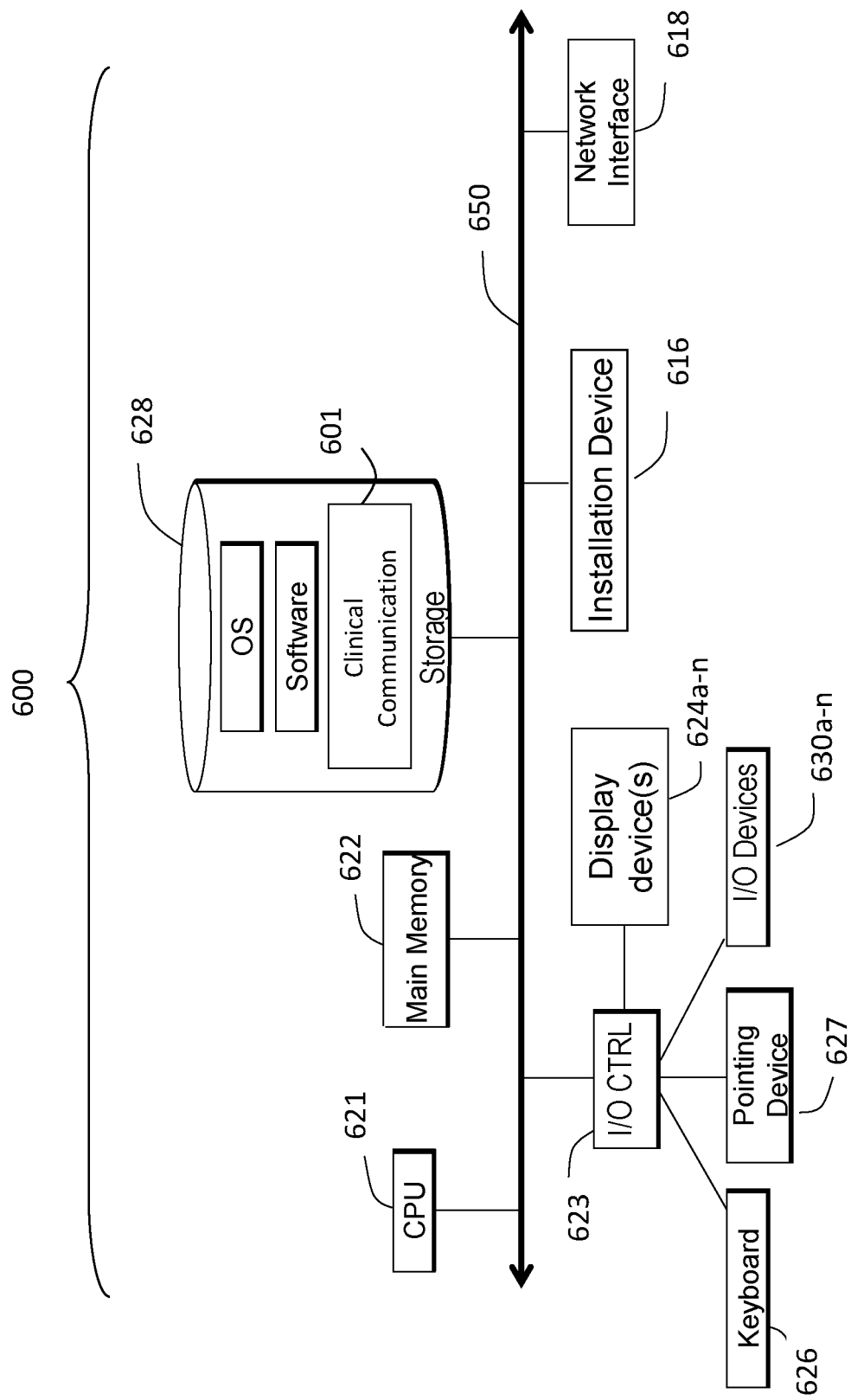
FIGS. 6A-6B are block diagrams of an embodiment of a computing environment for providing a clinical communication platform with real-time collaboration.
Figure 6B:
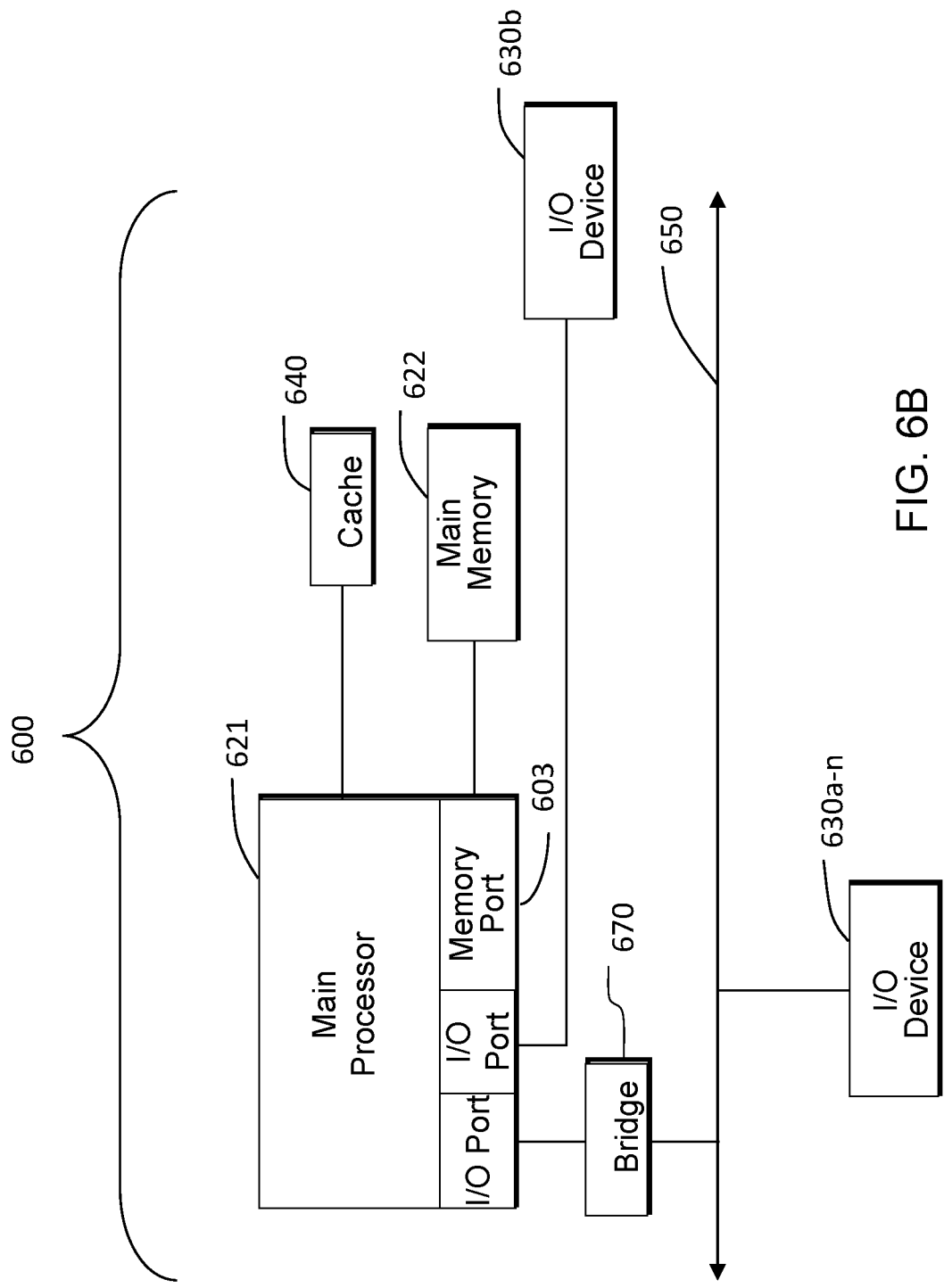

III. Computing Environments for Providing a Clinical Communication Platform with Real-Time Collaboration FIGS. 6A and 6B depict block diagrams of a computing device 600. As shown in FIGS. 6A and 6B, each computing device 600 includes a central processing unit 621, and a main memory unit 622. As shown in FIG. 6A, a computing device 600 can include a storage device 628, an installation device 616, a network interface 618, an I/O controller 623, display devices 624a-624n, a keyboard 626 and a pointing device 627, e.g. a mouse. The storage device 628 can include, without limitation, an operating system, software, and software of the clinical communication platform 100. As shown in FIG. 6B, each computing device 600 can also include additional optional elements, e.g. a memory port 603, a bridge 670, one or more input/output devices 630a-630n (generally referred to using reference numeral 630), and a cache memory 640 in communication with the central processing unit 621.

The central processing unit 621 is any logic circuitry that responds to and processes instructions fetched from the main memory unit 622. In many embodiments, the central processing unit 621 is provided by a microprocessor unit, e.g. those manufactured by Intel Corporation of Mountain View, Calif.; those manufactured by Motorola Corporation of Schaumburg, Ill.; the ARM processor (from, e.g., ARM Holdings and manufactured by ST, TI, ATMEL, etc.) and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif.; or field programmable gate arrays ("FPGAs") from Altera in San Jose, Calif., Intel Corporation, Xlinix in San Jose, Calif., or MicroSemi in Aliso Viejo, Calif., etc. The computing device 600 can be based on any of these processors, or any other processor capable of operating as described herein. The central processing unit 621 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 622 can include one or more memory chips capable of storing data and allowing any storage location to be directly accessed by the microprocessor 621. Main memory unit 622 can be volatile and faster than storage 628 memory. Main memory units 622 can be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 622 or the storage 628 can be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 622 can be based on any of the above described memory chips, or any other available memory chips capable of operating as described herein. In the embodiment shown in FIG. 6A, the processor 621 communicates with main memory 622 via a system bus 650 (described in more detail below). FIG. 6B depicts an embodiment of a computing device 600 in which the processor communicates directly with main memory 622 via a memory port 603. For example, in FIG. 6B the main memory 622 can be DRDRAM.

FIG. 6B depicts an embodiment in which the main processor 621 communicates directly with cache memory 640 via a secondary bus, sometimes referred to as a backside bus. In other embodiments, the main processor 621 communicates with cache memory 640 using the system bus 650. Cache memory 640 typically has a faster response time than main memory 622 and is typically provided by SRAM, BSRAM, or EDRAM. In the embodiment shown in FIG. 6B, the processor 621 communicates with various I/O devices 630 via a local system bus 650. Various buses can be used to connect the central processing unit 621 to any of the I/O devices 630, including a PCI bus, a PCI-X bus, or a PCI-Express bus, or a NuBus. For embodiments in which the I/O device is a video display 624, the processor 621 can use an Advanced Graphics Port (AGP) to communicate with the display 624 or the I/O controller 623 for the display 624. FIG. 6B depicts an embodiment of a computer 600 in which the main processor 621 communicates directly with I/O device 630b or other processors 621' via HYPERTRANSPORT, RAPIDIO, or INFINIBAND communications technology. FIG. 6B also depicts an embodiment in which local busses and direct communication are mixed: the processor 621 communicates with I/O device 630a using a local interconnect bus while communicating with I/O device 630b directly.

A wide variety of I/O devices 630a-630n can be present in the computing device 600. Input devices can include keyboards, mice, trackpads, trackballs, touchpads, touch mice, multi-touch touchpads and touch mice, microphones (analog or MEMS), multi-array microphones, drawing tablets, cameras, single-lens reflex camera (SLR), digital SLR (DSLR), CMOS sensors, CCDs, accelerometers, inertial measurement units, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 630a-630n can include a combination of multiple input or output devices, including, e.g., Microsoft KINECT, Nintendo Wiimote for the WII, Nintendo WII U GAMEPAD, or Apple IPHONE. Some devices 630a-630n allow gesture recognition inputs through combining some of the inputs and outputs. Some devices 630a-630n provides for facial recognition which can be utilized as an input for different purposes including authentication and other commands. Some devices 630a-630n provides for voice recognition and inputs, including, e.g., Microsoft KINECT, SIRI for IPHONE by Apple, Google Now or Google Voice Search. In some embodiments, devices 630a-630n include autonomous reality and/or virtual reality functionality, such as by including transparent or translucent displays, e.g. Microsoft HOLOLENS, Samsung GEAR VR, or other such devices.

Additional devices 630a-630n have both input and output capabilities, including, e.g., haptic feedback devices, touchscreen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, can have larger surfaces, such as on a table-top or on a wall, and can also interact with other electronic devices. Some I/O devices 630a-630n, display devices 624a-624n or group of devices can be augmented reality devices. The I/O devices can be controlled by an I/O controller 621 as shown in FIG. 6A. The I/O controller 621 can control one or more I/O devices, such as, e.g., a keyboard 126 and a pointing device 627, e.g., a mouse or optical pen. Furthermore, an I/O device can also provide storage and/or an installation medium 46 for the computing device 600. In still other embodiments, the computing device 600 can provide USB connections (not shown) to receive handheld USB storage devices. In further embodiments, an I/O device 630 can be a bridge between the system bus 650 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 624a-624n can be connected to I/O controller 621. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g. stereoscopy, polarization filters, active shutters, or autostereoscopy. Display devices 624a-624n can also be a head-mounted display (HMD). In some embodiments, display devices 624a-624n or the corresponding I/O controllers 623 can be controlled through or have hardware support for OPENGL or DIRECTX API or other graphics libraries.

In some embodiments, the computing device 600 can include or connect to multiple display devices 624a-624n, which each can be of the same or different type and/or form. As such, any of the I/O devices 630a-630n and/or the I/O controller 623 can include any type and/or form of suitable hardware, software, or combination of hardware and software to support, enable or provide for the connection and use of multiple display devices 624a-624n by the computing device 600. For example, the computing device 600 can include any type and/or form of video adapter, video card, driver, and/or library to interface, communicate, connect or otherwise use the display devices 624a-624n. In one embodiment, a video adapter can include multiple connectors to interface to multiple display devices 624a-624n. In other embodiments, the computing device 600 can include multiple video adapters, with each video adapter connected to one or more of the display devices 624a-624n. In some embodiments, any portion of the operating system of the computing device 600 can be configured for using multiple displays 624a-624n. In other embodiments, one or more of the display devices 624a-624n can be provided by one or more other computing devices 600a or 600b connected to the computing device 600, via the network 640. In some embodiments software can be designed and constructed to use another computer's display device as a second display device 624a for the computing device 600. For example, in one embodiment, an Apple iPad can connect to a computing device 600 and use the display of the device 600 as an additional display screen that can be used as an extended desktop. One ordinarily skilled in the art will recognize and appreciate the various ways and embodiments that a computing device 600 can be configured to have multiple display devices 624a-624n.

Referring again to FIG. 6A, the computing device 600 can comprise a storage device 628 (e.g. one or more hard disk drives or redundant arrays of independent disks) for storing an operating system or other related software, and for storing application software programs such as any program related to the software for the CIVS 200. Examples of storage device 628 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 628 can be non-volatile, mutable, or read-only. Some storage device 628 can be internal and connect to the computing device 600 via a bus 650. Some storage device 628 can be external and connect to the computing device 600 via a I/O device 630 that provides an external bus. Some storage device 628 can connect to the computing device 600 via the network interface 618 over a network, including, e.g., the Remote Disk for MACBOOK AIR by Apple. Some client devices 600 can not require a non-volatile storage device 628 and can be thin clients or zero clients 202. Some storage device 628 can also be used as an installation device 616, and can be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Computing device 600 can also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc.

Furthermore, the computing device 600 can include a network interface 618 to interface to the network 640 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 600 communicates with other computing devices 600' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 48 can comprise a built-in network adapter, network interface card, PCMCIA network card, EXPRESSCARD network card, card bus network adapter, wireless network adapter, USB network adapter, modem or any other device suitable for interfacing the computing device 600 to any type of network capable of communication and performing the operations described herein.

A computing device 600 of the sort depicted in FIG. 6A can operate under the control of an operating system, which controls scheduling of tasks and access to system resources. The computing device 600 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 7000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, can be used on zero clients or thin clients, including, e.g., CHROMEBOOKS.

The computer system 600 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 600 has sufficient processor power and memory capacity to perform the operations described herein. In some embodiments, the computing device 600 can have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 600 is a gaming system. For example, the computer system 600 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, or an XBOX 360 device manufactured by the Microsoft Corporation of Redmond, Wash., or an OCULUS RIFT or OCULUS VR device manufactured BY OCULUS VR, LLC of Menlo Park, Calif.

In some embodiments, the computing device 600 is a digital audio player such as the Apple IPOD, IPOD Touch, and IPOD NANO lines of devices, manufactured by Apple Computer of Cupertino, Calif. Some digital audio players can have other functionality, including, e.g., a gaming system or any functionality made available by an application from a digital application distribution platform. For example, the IPOD Touch can access the Apple App Store. In some embodiments, the computing device 600 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 600 is a tablet e.g. the IPAD line of devices by Apple; GALAXY TAB family of devices by Samsung; or KINDLE FIRE, by Amazon.com, Inc. of Seattle, Wash. In other embodiments, the computing device 600 is an eBook reader, e.g. the KINDLE family of devices by Amazon.com, or NOOK family of devices by Barnes & Noble, Inc. of New York City, N.Y.

In some embodiments, the communications device 600 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 600 is a laptop or desktop computer equipped with a web browser and a microphone and speaker system, e.g. a telephony headset. In these embodiments, the communications devices 600 are web-enabled and can receive and initiate phone calls. In some embodiments, a laptop or desktop computer is also equipped with a webcam or other video capture device that enables video chat and video call.

In some embodiments, the status of one or more machines 600 in the network are monitored, generally as part of network management. In one of these embodiments, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A system, comprising:
   an image capture device configured to detect a plurality of images of a subject; and
   one or more processors configured to:
   receive the plurality of images;
   identify the subject using the plurality of images;
   detect a movement of the subject using the plurality of images;

compare the movement to a predetermined movement pattern corresponding to at least one of a functional reach, a sit to stand, or a timed up and go movement;
generate a movement metric based on the comparison; and
store, in a database, an association between a subject profile corresponding to the identified subject, the plurality of images, and the movement metric.

2. The system of claim 1, wherein the one or more processors are further configured to:
retrieve a subject assessment data structure corresponding to the identified subject, the subject assessment data structure comprising a plurality of fields;
identify at least one field of the plurality of fields corresponding to the movement;
generate an indication of the movement comprising at least one text string; and
assign the indication of the movement to the identified at least one field.

3. The system of claim 1, wherein the one or more processors are further configured to:
retrieve, from the database, one or more previous images representing a previous functional reach, sit to stand, or timed up and go movement of the subject; and
generate a visual representation comparing the movement to the previous functional reach, sit to stand, or timed up and go movement of the subject using the one or more previous images.

4. The system of claim 1, wherein the one or more processors are further configured to apply a diagnosis function to the movement metric to generate a diagnosis regarding the subject.

5. The system of claim 1, wherein the one or more processors are further configured to provide a plurality of instructions regarding an assessment corresponding to the movement.

6. The system of claim 5, wherein the one or more processors are further configured to adjust the plurality of instructions based on the movement metric.

7. The system of claim 1, wherein the one or more processors are further configured to predict completion of a target condition of the subject corresponding to the movement based on the movement metric.

8. The system of claim 1, wherein the one or more processors are further configured to provide one or more therapy parameters based on the movement metric.

9. The system of claim 1, wherein the one or more processors are further configured to identify the predetermined movement pattern based on at least one of a functional reach test parameter, a sit to stand test parameter, or a timed up and go parameter.

10. The system of claim 1, wherein the one or more processors are further configured to detect the movement by identifying, from the plurality of images, at least one subset of pixels of the plurality of images corresponding to target features of the subject, and tracking the at least one subset of pixels across the plurality of images.

11. A method, comprising:
detecting, by an image capture device, a plurality of images of a subject;
receiving, by one or more processors, the plurality of images;
identifying, by the one or more processors, the subject using the plurality of images;
detecting, by the one or more processors, a movement of the subject using the plurality of images;
comparing, by the one or more processors, the movement to a predetermined movement pattern corresponding to at least one of a functional reach, a sit to stand, or a timed up and go movement;
generating, by the one or more processors, a movement metric based on the comparison; and
storing, by the one or more processors in a database, an association between a subject profile corresponding to the identified subject, the plurality of images, and the movement metric.

12. The method of claim 11, further comprising:
retrieving a subject assessment data structure corresponding to the identified subject, the subject assessment data structure comprising a plurality of fields;
identifying at least one field of the plurality of fields corresponding to the movement;
generating an indication of the movement comprising at least one text string; and
assigning the indication of the movement to the identified at least one field.

13. The method of claim 11, further comprising:
retrieving, from the database, one or more previous images representing a previous functional reach, sit to stand, or timed up and go movement of the subject; and
generating a visual representation comparing the movement to the previous functional reach, sit to stand, or timed up and go movement of the subject using the one or more previous images.

14. The method of claim 11, further comprising applying a diagnosis function to the movement metric to generate a diagnosis regarding the subject.

15. The method of claim 11, further comprising providing a plurality of instructions regarding an assessment corresponding to the movement.

16. The method of claim 15, further comprising adjusting the plurality of instructions based on the movement metric.

17. The method of claim 11, further comprising predicting completion of a target condition of the subject corresponding to the movement based on the movement metric.

18. The method of claim 11, further comprising providing one or more therapy parameters based on the movement metric.

19. The method of claim 11, further comprising identifying the predetermined movement pattern based on at least one of a functional reach test parameter, a sit to stand test parameter, or a timed up and go parameter.

20. The method of claim 11, further comprising detecting the movement by identifying, from the plurality of images, at least one subset of pixels of the plurality of images corresponding to target features of the subject, and tracking the at least one subset of pixels across the plurality of images.

* * * * *